(12) United States Patent
Houben

(10) Patent No.: US 7,412,282 B2
(45) Date of Patent: Aug. 12, 2008

(54) ALGORITHMS FOR DETECTING CARDIAC ARRHYTHMIA AND METHODS AND APPARATUSES UTILIZING THE ALGORITHMS

(75) Inventor: Richard P. M. Houben, Lanaken (BE)

(73) Assignee: Medtronic, Inc., Minneapolis, MN (US)

( * ) Notice: Subject to any disclaimer, the term of this patent is extended or adjusted under 35 U.S.C. 154(b) by 510 days.

(21) Appl. No.: 11/043,584

(22) Filed: Jan. 26, 2005

(65) Prior Publication Data

US 2006/0167364 A1 Jul. 27, 2006

(51) Int. Cl.
*A61B 5/0402* (2006.01)
(52) U.S. Cl. .......................... 600/515; 607/5
(58) Field of Classification Search ......... 600/509–518; 607/5, 14
See application file for complete search history.

(56) References Cited

U.S. PATENT DOCUMENTS

| | | | |
|---|---|---|---|
| 5,265,617 A | 11/1993 | Verrier et al. | |
| 5,560,369 A * | 10/1996 | McClure et al. | 600/518 |
| 5,987,352 A | 11/1999 | Klein et al. | |
| 6,230,059 B1 | 5/2001 | Duffin | |
| 2003/0050565 A1 | 3/2003 | Couderc et al. | |
| 2004/0092836 A1 | 5/2004 | Ritscher et al. | |
| 2004/0171954 A1 | 9/2004 | Holman | |
| 2004/0176697 A1 | 9/2004 | Kappenberger et al. | |
| 2004/0210147 A1 | 10/2004 | Houben | |

FOREIGN PATENT DOCUMENTS

WO WO9802209 1/1998

OTHER PUBLICATIONS

Hnatkova K. et al: "Numeric processing of Lorenz plots of R-R intervals from long-term ECGs", Journal of Electrocardiology, vol. 28, 1995, pp. 74-80.
Knaf H et al.: "Risikoabschaetzung fuer die Erkrankung an Herzrhythmusstoerujngen/Ploetzlichem Hertztod", Dec. 17, 2001.

* cited by examiner

*Primary Examiner*—Scott M Getzow
(74) *Attorney, Agent, or Firm*—Paul H. McDowall; Michael C. Soldner; Steve Bauer

(57) ABSTRACT

A method for detecting a cardiac arrhythmia from an electrocardiogram includes the steps of identifying a plurality of R-waves in the electrocardiogram during a predetermined time interval; extracting heartbeat complexes corresponding to the identified R-waves; identifying a key region within each heartbeat complex that is morphologically altered in the event of the cardiac arrhythmia; calculating a statistical measurement of an ensemble of the key regions from each of the heartbeat complexes; and determining from the statistical measurement whether the cardiac arrhythmia occurred during the predetermined time interval. An apparatus is also provided that includes a processor that is coupled to receive an electrocardiogram, and is configured in response thereof to perform the method for detecting a cardiac arrhythmia.

38 Claims, 7 Drawing Sheets

ALGORITHMS FOR DETECTING CARDIAC ARRHYTHMIA AND METHODS AND APPARATUSES UTILIZING THE ALGORITHMS

FIELD

The present invention generally relates to methods for detecting abnormal heart rhythms in patients, and more particularly relates to methods and systems that implement morphological analysis of electrograms to detect atrial fibrillation in patients.

BACKGROUND

Atrial fibrillation (AF) is a condition during which there is disorganized electrical conduction in the atria, resulting in ineffective pumping of blood into the ventricle. If AF is detected, pharmacological cardioversion medication and electrical cardioversion are often effective at restoring and maintaining sinus rhythm. However, half of the recurrent episodes of AF are asymptomatic or "silent" and consequently can go undetected by a patient or physician. It is important to detect even asymptomatic AF because asymptomatic periods contribute to continued stroke risk and atrial remodeling.

Until recently, real time analysis of an intra-cardiac electrogram (EGM) has been based on coupling cardiac event detection with at least one algorithm that makes determinations based on sensed intervals. Generally, sensing cardiac events includes the reduction of information contained in the EGM to a binary event that signals the occurrence of atrial or ventricular activation. A sequence of such binary events is subsequently used to detect an abnormality, such as AF, by applying a process that analyzes a time relationship between the sensed binary events and triggers prescribed therapies based on the time relationship.

The introduction of real-time digital signal processing technology in implantable devices has added new dimensions to cardiac signal analysis. In addition to event based processing, digital signal processing technology enables morphological analysis of an EGM. There is great potential for the application of digital signal processing technology to combine algorithms based on morphological analysis with established event based algorithms to analyze cardiac signals and provide an early determination that asymptomatic AF is occurring with a patient.

Accordingly, it is desirable to provide a method and apparatus that enable detection of AF in patients, and particularly in patients that in which AF may be recurring. In addition, it is desirable to provide a method and apparatus that combines morphological analysis algorithms with event based analysis algorithms to enable detection of AF in patients. Furthermore, other desirable features and characteristics of the present invention will become apparent from the subsequent detailed description and the appended claims, taken in conjunction with the accompanying drawings and the foregoing technical field and background.

BRIEF SUMMARY

According to one aspect of the invention, a method is provided for detecting a cardiac arrhythmia from an electrocardiogram. The method includes the steps of identifying a plurality of wave patterns that are repeated in the electrocardiogram during a predetermined time interval, each wave pattern being indicative of an individual heartbeat; extracting heartbeat complexes corresponding to the identified wave patterns; identifying a key region within each heartbeat complex that is morphologically altered in the event of the cardiac arrhythmia; calculating a statistical measurement of an ensemble of the key regions from each of the heartbeat complexes; and determining from the statistical measurement whether the cardiac arrhythmia occurred during the predetermined time interval.

An apparatus is also provided that includes a processor that is coupled to receive an electrocardiogram, and is configured in response thereof to perform the method for detecting a cardiac arrhythmia.

BRIEF DESCRIPTION OF THE DRAWINGS

The present invention will hereinafter be described in conjunction with the following drawing figures, wherein like numerals denote like elements.

FIG. 6 is a graph representing signal averaged P-wave analysis of an ECG;

DESCRIPTION

The following description is merely exemplary in nature and is not intended to limit the invention or the application and uses of the invention. Furthermore, there is no intention to be bound by any expressed or implied theory presented in the preceding technical field, background, brief summary or the following detailed description.

The present invention introduces a multi resolution signal-processing framework that implements digital signal processing technology into Arrhythmia detection processes that include event-based analysis algorithms. By combining digital signal processing technology with event-based algorithms, an EGM can be unraveled and normal patterns can be discriminated from AF patterns by focusing on wave morphology using wavelet multi-resolution analysis (MRA). Wavelet MRA concerns morphology at the intra-wave level, and provides a level of EGM detail. However, the principles of the present invention can be applied to coarser details, including morphology at the inter-wave scale, the intra-complex scale, and perhaps even coarser scales such as the inter-complex, intra-episode, and intra-episode scales.

Figure 1:
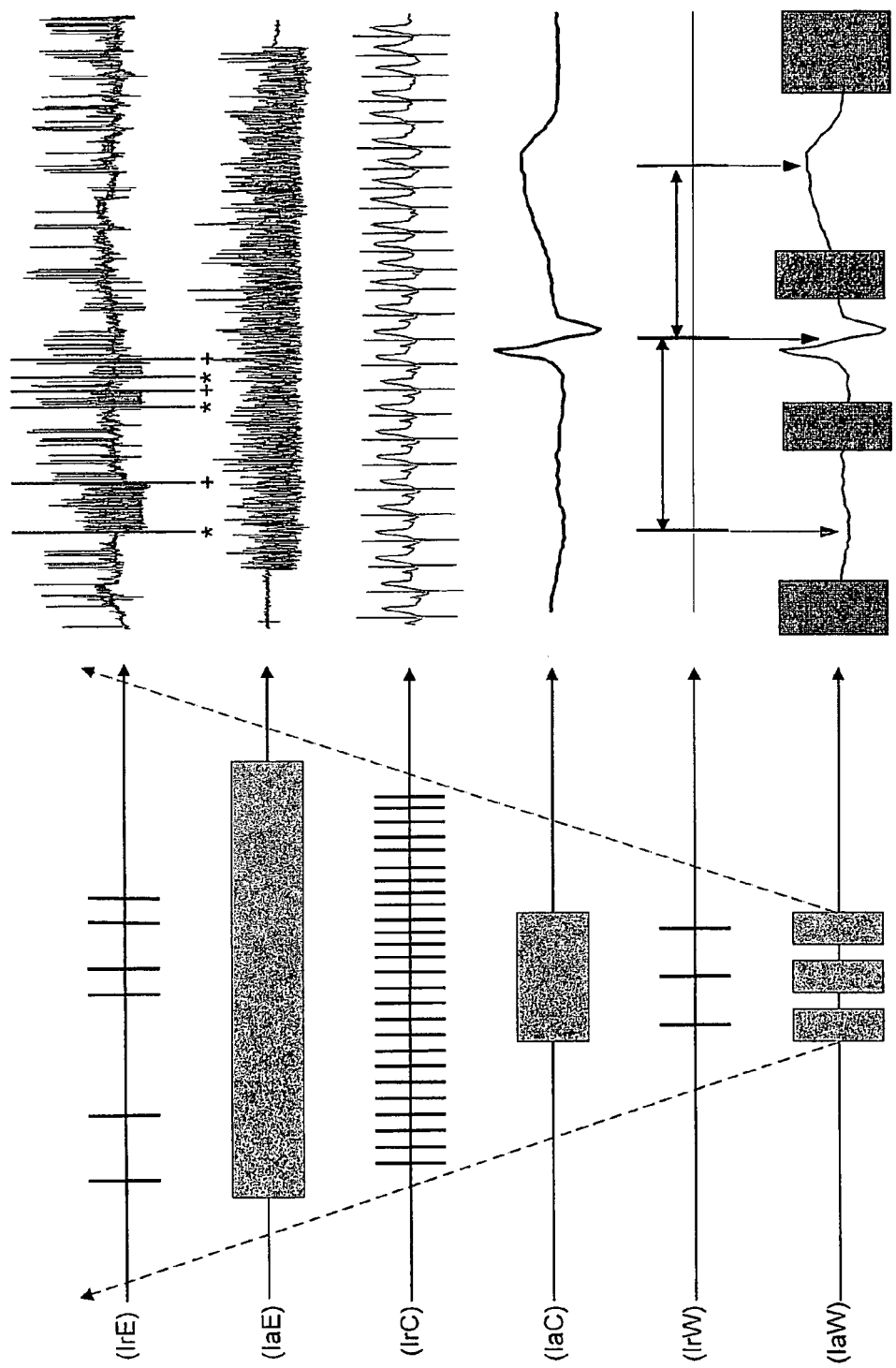
FIG. 1 is a chart that depicts a multi-resolution analysis framework alongside examples of EGMs that typify the inputs for analysis at each respective analysis level.

Before describing the aspects of the invention involving intra-wave analysis, other analysis levels will be briefly summarized since the present invention couples analysis at the intra-wave level with algorithms that fall in the framework of other analytical levels. FIG. 1 is a chart that depicts MRA framework generally, alongside examples of EGMs that typify the inputs for analysis at each respective analysis level. Starting at the top of the chart, a twenty-four hour RR interval sequence EGM is illustrated as an inter-episode (IrE) analysis example. Next, an RR interval sequence representing an episode of AF is illustrated as an intra-episode (IaE) analysis example. Next, a sequence of ECG complexes signifying the transition from normal sinus rhythm to AF is illustrated as an input for inter-complex (IrC) analysis. A single complex is illustrated next as an example input for intra-complex (IaC) analysis, and the timing of the P, QRS, and T wave appearances are marked within the same complex to illustrate inter-wave (IrW) analysis. Finally, the morphology of the P, QRS, and T waves is scrutinized at the finest level of analysis which is the intra-wave (IaW) level.

Figure 2:
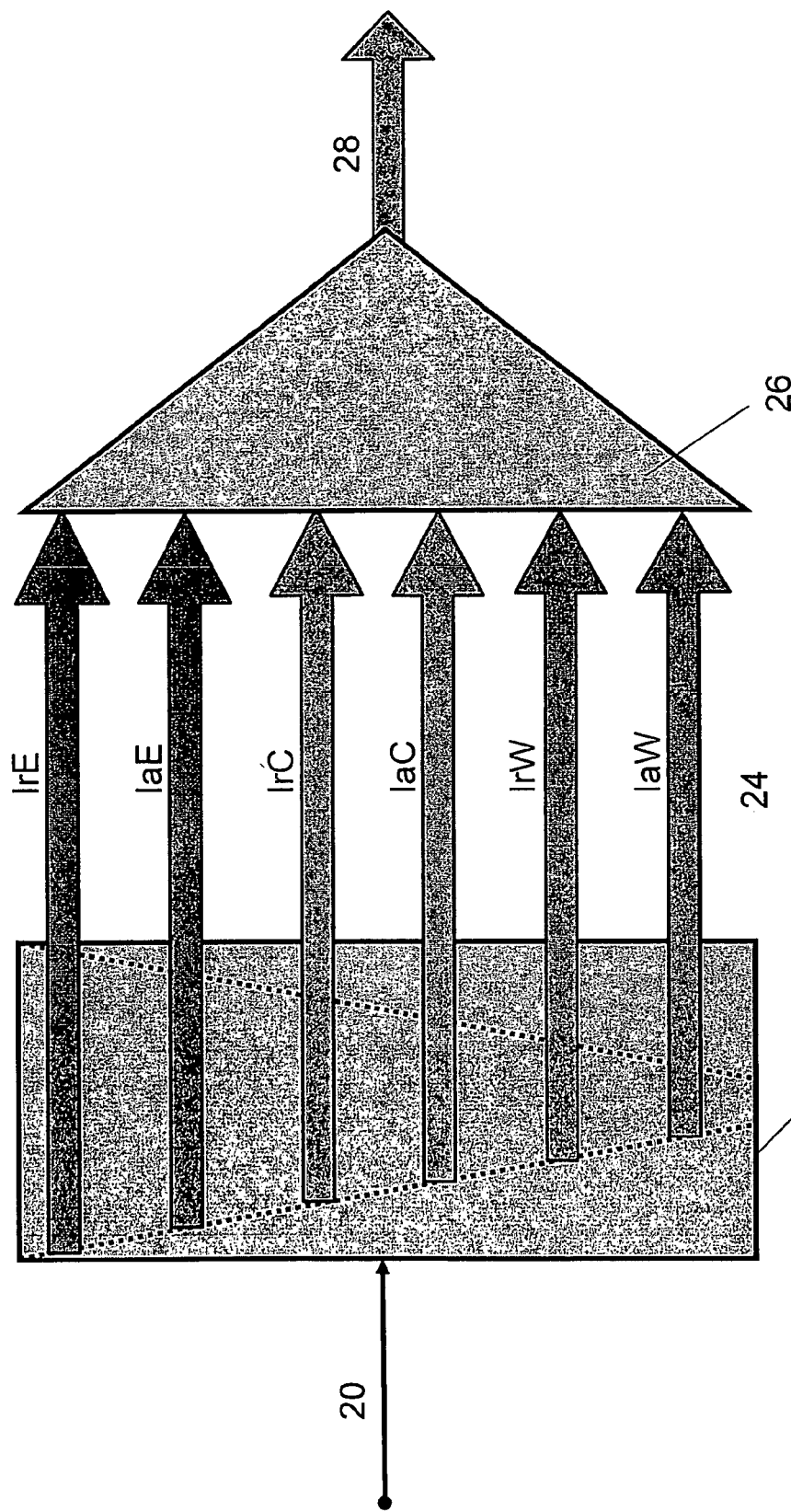
FIG. 2 is a diagram that illustrates a combination of multi-resolution analyses beginning with an EGM signal and ending with a decision vector based on the combined analyses according to the present invention.

As previously mentioned, the present invention utilizes digital signal processing to combine event-based algorithms with morphological algorithms. According to an exemplary embodiment, the morphological analysis is performed at the intra-wave level, while event-based analysis is performed at a coarser level such as the inter-complex level. In order to combine the analyses, the EGM is converted into a set of characterization vectors or "EGM fingerprints" representing analysis results from each time scale. FIG. 2 is a diagram that illustrates the combination of the analyses starting from the EGM signal 20 and ending with a decision vector 28. Performance of MRA 22 for each time scale produces characterization vectors 24 that are input into an inference engine 26. The inference engine 26 combines all characterization vectors into the decision vector 28 that contains diagnostic information and certainty levels. The decision vector 28 is a single diagnostic parameter that can be used to automatically control a therapy, trigger internal storage of signals, generate a physician or patient alarm, and perform other procedures based on the information. Inference methods may include programmed decision trees or may rely on more complex methods like Bayesian networks and other probabilistic models, fuzzy logic, or neural networks.

Having described various EGM analysis levels and the manner by which the analyses can be combined, intra-wave analysis according to the present invention will next be described. Like many types of signals, EGMs are analyzed by examining regions that include sharp deflections or singularities. Wavelet MRA is well adapted to characterize EGM singularities by decomposing the EGM into signal components at different time scales and event segment or fractures. According to one embodiment of the present invention, wavelet analysis primarily includes transformation of the EGM to the wavelet domain represented using a set of wavelet coefficients. It should be understood that the following wavelet analysis procedure is only one of many possible procedures by which analysis can be performed according to the principles of the invention.

The wavelet transformation is based on comparison of the signal with a family of test functions or wavelets derived from a single function called the mother wavelet. The mother wavelet $\Psi$ is a normalized, finite energy, zero average function centered round t=0. A family of wavelets is then obtained by scaling and translation of the mother wavelet $\Psi$:

$$\Psi_{u,s}(t) = \frac{1}{\sqrt{s}} \Psi\left(\frac{t-u}{s}\right), \qquad (1)$$

with s being the scaling parameter controlling the support of the wavelet and u being the translation parameter. Like a windowed Fourier transform (STFT)[6], the wavelet transform measures time-frequency variations of spectral components. The wavelet transform is defined as the convolution sum of the EGM and the family of wavelets. For an electrogram E the wavelet transform at time u and scale s is defined as:

$$WE(u, s) = \langle E, \Psi_{u,s} \rangle = \int_{-\infty}^{\infty} E(t)\Psi^*\left(\frac{t-u}{s}\right)dt. \qquad (2)$$

With a decrease of the scale s, the support of the wavelet shrinks (compression) and the wavelet transform becomes more sensitive to fine details of the EGM. Increasing the scale parameter reveals the overall structure or skeleton of the wave.

Wavelet MRA is based on linking the characteristics of the EGM obtained by progressive reduction of the wavelet scaling parameter. A large amplitude wavelet coefficient is created by selecting a suitable mother wavelet and identifying a desired singularity such as a sharp signal transition. Sharp transitions are detected by tracking local maxima across the scales of the wavelet transform. High amplitude wavelet coefficients indicate the position of sharp variations in image intensity, referred to as edges. Further, MRA enables discrimination between different types of edges by performing a measurement of the regularity at which the edges appear. The relation between the decay of the wavelet maxima and local signal regularity has been described in detail by S. Mallat, *A Wavelet Tour of Signal Processing*, 1998 (Academic Press) which is incorporated herein by reference. Different scales provide the contours of image structures of varying sizes that are particularly effective for EGM wave pattern recognition.

Figure 3:
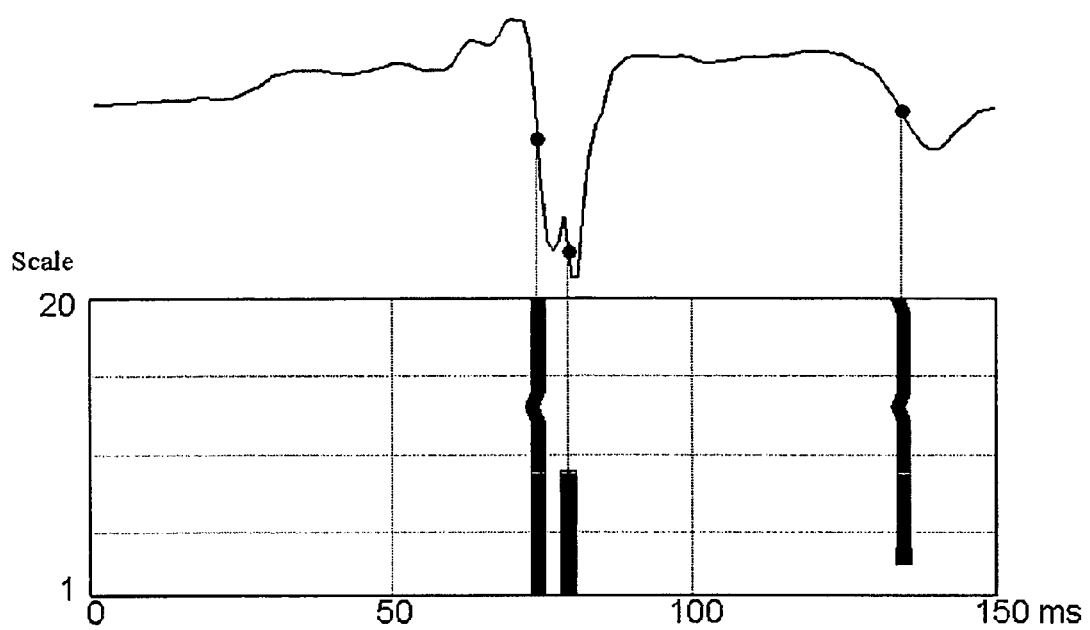
FIG. 3 is a unipolar EGM positioned above a time-scale plane showing trajectories of three local maxima lines obtained by successive chaining of wavelet coefficients.

An example of multi-resolution wavelet analysis of a unipolar EGM recorded from the epicardial lateral wall of the right atrium is given in FIG. 3. The EGM illustrates three fibrillation waves characterized by wavelet MRA. The EGM is positioned in FIG. 3 above a time-scale plane depicting trajectories of three local maxima lines obtained by successive chaining of wavelet coefficients. In this example, the first derivative of a Gaussian was used as the mother wavelet:

$$\Theta(t) = C_p e^{-t^2}, \qquad (3)$$

$$\text{with } \Psi(t) = \frac{d}{dt}\Theta(t),$$

1 being the Gaussian function, and $\Theta$ being the mother wavelet.

The regularity of the EGM is related to the persistence of local maxima over the scales starting from the finest scale (1) towards the coarsest scale (20) and vice versa. An iterative chaining process of local maxima is used to determine the length of the trajectory of local maxima over the scales. During this analysis, the maximum deviation in time of local maxima in two adjacent scales was not allowed to deviate more than 2 ms. Violation of this criterion terminated the chaining process. At each time instance (1 ms), the length of the trajectory of maxima (number of scales) was taken as the measure of regularity of the EGM. Indeed, the main deflection generated local maxima over all 20 scales, and the small notch directly following the main deflection was associated with maxima line that persisted only from scale 1 to 9. Although a local maxima line is also produced by the ventricular far-field potential (100-150 ms), the EGM associated with this phenomenon is more regular since the local maxima line does not persist up to the finest scale (1).

Having described algorithms for transforming the EGM to the wavelet domain, a series of two algorithms will next be described for detecting AF in a patient. The first of the two algorithms is commonly referred to as the cluster signature metric (CSM) method and is described in detail in U.S. Patent Application Publication No. 20040092836, by D. Ritscher et al. and assigned to Medtronic, Inc. which is hereby incorporated herein by reference.

Although the CSM method is described in detail in the Ritscher publication, a general overview of the method will now be described. Atrial arrhythmias including AF and atrial flutter (AFL) are detected within a segment of ventricular heartbeats signified by intervals between successive ventricular heartbeats that exhibit discriminatory signatures when plotted as data points in a scatter-plot. The first step of the method includes defining an AF signature metric for AF representative of the sparse distribution of data points during AF episodes. To distinguish AF from AFL, the method further includes the step of defining an AFL signature metric representative of the clustering distribution of data points during AFL episodes. Next, an interval is defined between successive ventricular heartbeats. Each succeeding interval is then plotted as a data point in a scatter-plot. After preparing the scatter-plot, a discriminatory metric is developed that signifies the degree of sparseness or clustering of the scatter-plot data points. It is determined that AF occurred if the discriminatory metric satisfies the AF signature metric representative of the distribution of data points during AF. Likewise, it is determined that AFL occurred if the discriminatory metric satisfies the AFL signature metric representative of the distribution of data points during AFL.

In an exemplary embodiment of the invention, the step of defining the interval between successive ventricular heartbeats includes determining the change between each succeeding interval between consecutive heartbeats. Then, a Lorenz plot is prepared as the scatter-plot. An abscissa value and an ordinate value (referenced to the Lorenz plot origin) to each 2-D data point. Then, 2-D bins of the Lorenz plot are defined with reference to the Lorenz plot origin, and each 2-D point is correlated with a bin of the Lorenz plot in which the 2-D data point falls.

In a more specific embodiment of the invention, the step of developing a discriminatory metric is performed by counting the number of 2-D data points added to each bin over a segment, determining the highest number of 2-D data points in a single bin, counting the number of bins containing at least one 2-D data point, counting the number of bins containing at least one 2-D data point and a predetermined number of 2-D data points, and from these determinations and counts calculating the CSM.

In an even more specific embodiment, AF is detected based on measurement of variability of the intervals between sensed R-waves. For example, following detection of R-waves for a predetermined interval, an RR-variability histogram is created. After a two minute detection interval, a histogram (−600 ms to +600 ms; 40 ms bins) is created from two subsequent pairs of RR-interval differences. Next, the CSM, referred to in this case as the AF-index, is calculated from the three parameters extracted from the histogram and discussed above, as follows:

$$AF_{idx} = nozC + lowC - maxB \qquad (4)$$

with nozC representing the number of histogram bins that have been addressed at least once during two minutes, lowC representing the number of bins addressed at least once but less then six times, and maxB representing the value of the highest count in the histogram. $AF_{idx}$ will have a high value during episodes of AF since both nozC and lowC will increase due to the heterogeneous character of the histogram during atrial fibrillation. In contrast the value of maxB will be low since no dominant RR-interval will be found during AF. Finally, detection of atrial fibrillation is realized by comparison of $AF_{idx}$ against a predefined threshold. An application of the CSM algorithm is provided in the following example.

EXAMPLE 1

For this study a data set of 24 hr. Holter recordings was used. The Holter dataset (15 patients) included both episodes of sinus rhythm, paroxysmal and persistent AF. The entire dataset was automatically annotated by the Marquette MARS® system (Version 4.1 a) indicating R-waves and the onset and termination of AF. Automatic annotations were subsequently edited by a trained physician. The entire set was divided into 10,637 episodes of two-minutes each containing three ECG signals (mod. $V_1$, $V_5$ aVF; sample frequency=128 Hz) and RR-intervals (2,339 episodes of AF, 8,215 episodes of sinus rhythm). A small percentage (0.78%) of all episodes included a fraction of AF between 30 and 90 s. Those episodes contained either very short paroxysms of AF or coincided with the onset or termination of AF, and both were excluded from analysis.

The result of the CSM algorithm detection performance for atrial fibrilation is summarized in Table I below. Performance was determined by calculating the sensitivity and specificity of detection results against annotations. An exact match of test and annotation data resulted in an average sensitivity (Se) of 93% and specificity (Sp) of 95% whereas allowing a detection deviation of ±1 episode (2 min) vs. expert annotation, the average Se/Sp increased to 98.8% and 97.1% (Table I). The $AF_{index}$ detection threshold was fixed at 100 in both cases.

TABLE I

Holter CSM analysis results

| HOLTER RECORDING | AF [%] | NUMBER OF EPISODES | TRUE POSITIVE | TRUE NEGATIVE | FALSE POSITIVE | FALSE NEGETIVE | SENSITIVITY [%] | SPECIFICITY [%] |
|---|---|---|---|---|---|---|---|---|
| 2 | 8 | 716 | 50 | 663 | 0 | 0 | 100 | 100 |
| 3 | 0 | 716 | 0 | 716 | 0 | 0 | — | 100 |

TABLE I-continued

Holter CSM analysis results

| HOLTER RECORDING | AF [%] | NUMBER OF EPISODES | TRUE POSITIVE | TRUE NEGATIVE | FALSE POSITIVE | FALSE NEGETIVE | SENSITIVITY [%] | SPECIFICITY [%] |
|---|---|---|---|---|---|---|---|---|
| 7  | 3   | 705 | 18  | 683 | 2   | 0 | 100  | 99.7 |
| 9  | 61  | 716 | 456 | 260 | 0   | 0 | 100  | 100  |
| 11 | 36  | 716 | 252 | 464 | 0   | 0 | 100  | 100  |
| 12 | 3   | 665 | 11  | 608 | 8   | 1 | 91.7 | 98.7 |
| 15 | 100 | 716 | 716 | 0   | 0   | 0 | 100  | —    |
| 17 | 0   | 714 | 0   | 698 | 16  | 0 | —    | 97.8 |
| 18 | 38  | 716 | 267 | 449 | 0   | 0 | 100  | 100  |
| 19 | <1  | 716 | 1   | 708 | 6   | 0 | 100  | 99.2 |
| 20 | 62  | 716 | 487 | 228 | 0   | 0 | 100  | 100  |
| 22 | 0   | 718 | 0   | 487 | 229 | 0 | —    | 68   |
| 24 | 13  | 718 | 72  | 582 | 21  | 3 | 96   | 96.5 |
| 26 | <1  | 655 | 0   | 653 | 0   | 0 | —    | 100  |
| 27 | 0   | 712 | 0   | 710 | 0   | 0 | —    | 100  |

Average sensitivity 98.8%
Average specificity 97.1%

The second of the two algorithms for detecting AF in a patient measures the power of P-waves that are synchronous to ventricular activation and that correspond to the R-waves analyzed during the CSM method. The power of each P-wave is determined using a hook that is found at the intra-wave level. The P-waver power algorithm is used to determine whether a P-wave is actually present since a phenomenon observed in an ECG during atrial fibrillation is the absence of a clear P-wave preceding the QRS complex. Instead of a distinct P-wave preceding the QRS complex, the ECG reveals small amplitude variations of the baseline that are not related to the R-wave. The P-wave power algorithm creates a parameter that discriminates between normal sinus rhythm and AF, and is based on analysis of a signal averaged (SA) ECG. The SAECG is created using the R-wave as a reference point trigger for averaging subsequent complexes.

Figure 4:
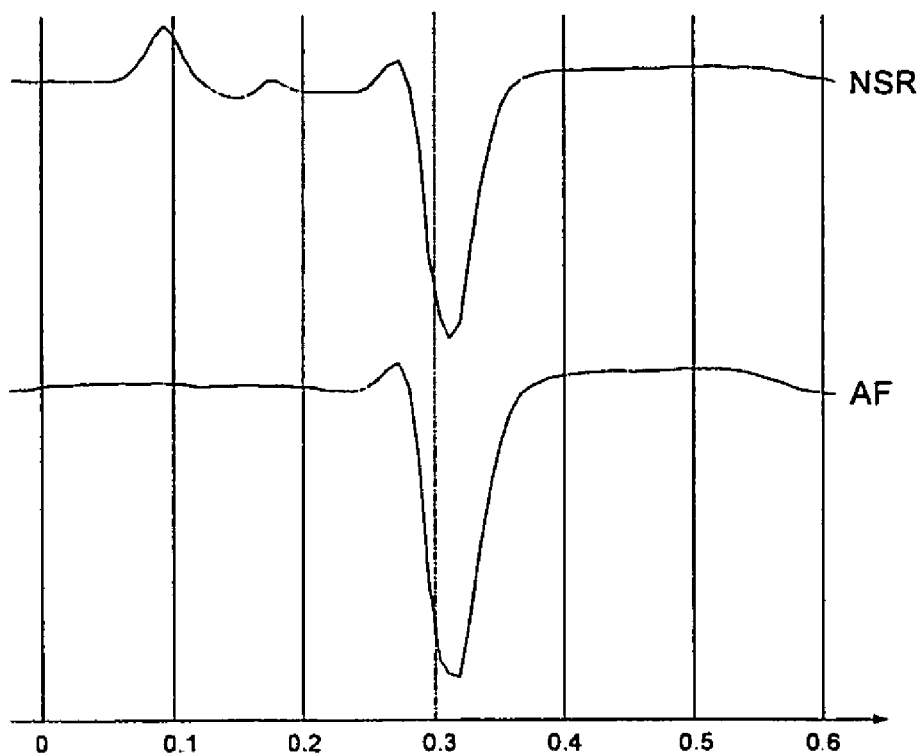
FIG. 4 is a graph of two signal-averaged ECG regions with each having an R-wave as a point of reference, with the top region representing SAECG waves captured during normal sinus rhythm (NSR), and the bottom signal-averaged region representing SAECG waves captured during AF.

In contrast to synchronous activation of the ventricles, during asynchronous rhythms such as those associated with AF the P-waves in the SAECG completely cancel out. FIG. 4 is a graph of two signal-averaged ECG regions with each having an R-wave as a point of reference. The top region represents SAECG waves captured during normal sinus rhythm (NSR), and the bottom signal-averaged region represents SAECG waves captured during AF. For each SAECG, any P-wave presence would be found in the time frame between 0.0 and 0.2 s. The reasons that the P-waves in the SAECG during AF cancel out are because of the P-waves' low amplitudes, and because the P-waves appear asynchronously with respect to the R-wave. Since the low amplitude P-waves do not precede the R-wave at exactly the same respective times during AF, a P-wave will not appear in a graph of a group of averaged ECGs.

Figure 5:
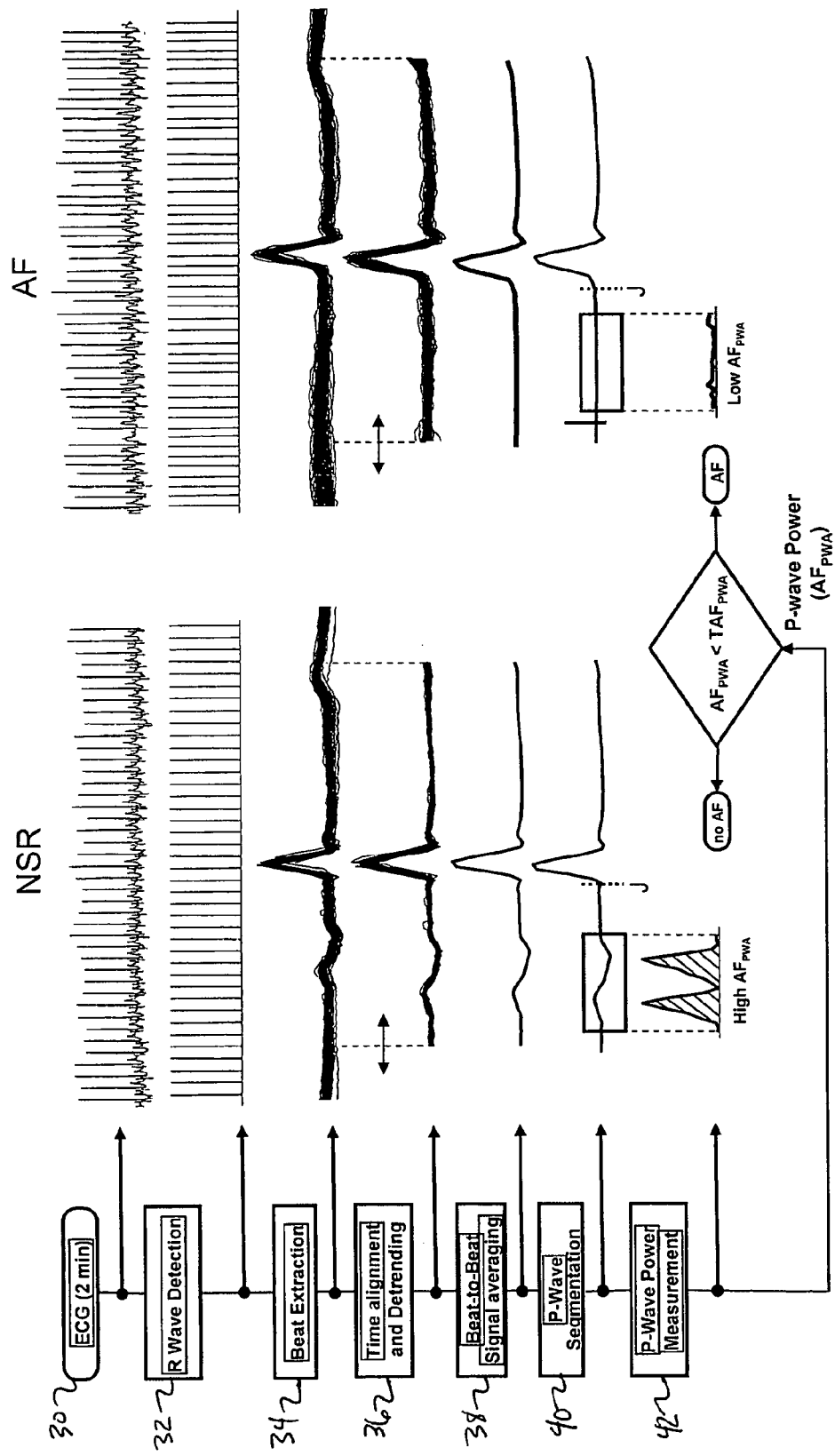
FIG. 5 is a flowchart that sets forth a process of averaging an ECG and thereby detecting AF according to the present invention.
Figure 9:
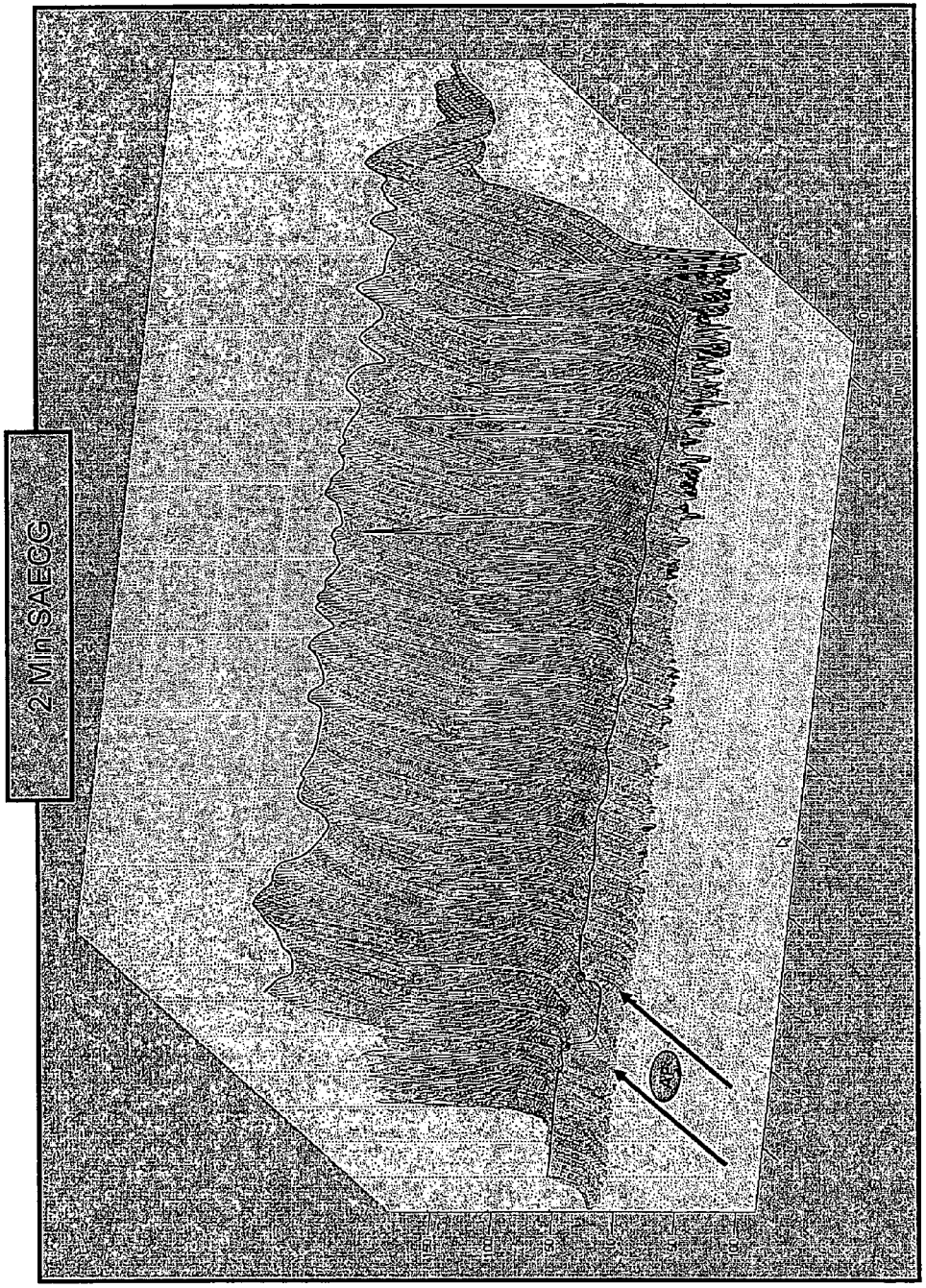

The process of averaging an ECG and thereby detecting AF will now be described with reference to the flowchart illustrated in FIG. 5. Signal averaging is performed by first receiving an ECG signal, represented as step 30, and simultaneously or thereafter detecting R-waves, represented as step 32, during a predetermined time interval. Next, a series of beat complexes around the detected R-waves are extracted, represented as step 34. The complexes should at least capture the area in which P-waves would be produced during normal sinus rhythm. The extracted series includes several complexes in an exemplary embodiment of the invention, although it should be recognized that the complexes do not necessarily need to be taken from consecutive beats. Before making any statistical calculations, in step 36 all of the extracted complexes are de-trended and band-pass filtered to remove further low frequency fluctuations of the baseline. Next, the ensemble average is calculated for each of the predetermined time intervals of the extracted complexes and this is represented as step 38. P-waves are then segmented, represented as step 40. Finally, the P-waver power within each averaged ECG is measured, represented as step 42 and described in greater detail later.

EXAMPLE 2

R-waves in the Holter ECGs from Example 1 were detected and captured during 2 min. episodes over a ~24-hour time period. Beat complexes around all of the detected R-waves were extracted, and all of the extracted complexes were de-trended using linear trend removal, and band-pass filtered using a Butterworth filter (−3 dB at 2.5 to 12 Hz) to remove further low frequency fluctuations of the baseline. The ensemble average was calculated for each of the two minute intervals of the extracted complexes. P-waves were then segmented. Finally, the P-waver power within each averaged ECG was measured. The P-waver power algorithm detection performance for AF is summarized in Table II. Performance was determined by calculating the sensitivity and specificity of detection results against annotations. An exact match of test and annotation data resulted in an average Se/Sp of 96.7% and 97.7% whereas allowing a deviation in detection of ±1 episode (two minutes) vs. expert annotation, the average Se/Sp was raised to 99.8% and 99.2% (Table II). The $AF_{index}$ detection threshold was fixed at 130.

TABLE II

Holter PWP analysis results

| HOLTER RECORDING | AF [%] | NUMBER OF EPISODES | TRUE POSITIVE | TRUE NEGATIVE | FALSE POSITIVE | FALSE NEGETIVE | SENSITIVITY [%] | SPECIFICITY [%] |
|---|---|---|---|---|---|---|---|---|
| 2  | 8   | 716 | 50  | 657 | 6  | 0 | 100  | 99.1 |
| 3  | 0   | 716 | 0   | 713 | 3  | 0 | —    | 99.6 |
| 7  | 3   | 705 | 18  | 667 | 18 | 0 | 100  | 97.4 |
| 9  | 61  | 716 | 448 | 260 | 0  | 8 | 98.3 | 100  |
| 11 | 36  | 716 | 252 | 464 | 0  | 0 | 100  | 100  |
| 12 | 3   | 665 | 12  | 616 | 0  | 0 | 100  | 100  |
| 15 | 100 | 716 | 716 | 0   | 0  | 0 | 100  | —    |
| 17 | 0   | 714 | 0   | 710 | 4  | 0 | —    | 99.4 |
| 18 | 38  | 716 | 267 | 449 | 0  | 0 | 100  | 100  |
| 19 | <1  | 716 | 1   | 710 | 4  | 0 | 100  | 99.4 |
| 20 | 62  | 716 | 487 | 221 | 7  | 0 | 100  | 96.9 |
| 22 | 0   | 718 | 0   | 712 | 4  | 0 | —    | 99.4 |
| 24 | 13  | 718 | 75  | 602 | 1  | 0 | 100  | 99.8 |
| 26 | <1  | 655 | 0   | 653 | 0  | 0 | —    | 100  |
| 27 | 0   | 712 | 0   | 692 | 18 | 0 | —    | 97.5 |

Average sensitivity 99.8%

Average specificity 99.2%

FIG. 6 is a graph representing signal averaged P-wave analysis on a patient's Holter recording. Consecutive signal averaged ECGs based on two minute episodes of ECG are represented in FIG. 6. The graph clearly shows that signal averaged P-waves disappear from the onset of AF (t=3:55 hrs.) and then recur at the onset of normal sinus rhythm (t=5:38 hrs.).

It is understood that the ECG episodes are not limited to two minute intervals as in the above example. The averaging period is variable in length and can be lengthened or shortened, trading off between detection accuracy and the detection parameter dynamic behavior as a result. Shorter averaging periods will provide higher dynamics since AF detection will potentially occur more quickly and updates will take place with greater frequency. However, shorter averaging periods may have a tendency to be less accurate than longer averaging periods. In an exemplary embodiment, a processor is configured to shorten the averaging periods if AF is detected.

Having described the CSM and P-wave power algorithms separately, a method of combining the algorithms according to an exemplary embodiment of the invention will be set forth next. Although either method acceptably discriminates between normal sinus rhythm and AF, a combination both methods may lead to even better results. Indeed, since the detailed results of the CSM and PWP algorithms shown in Tables I and II reveal that one of the algorithms has superior performance for some Holter recordings, an added value can be expected if the algorithms are combined. Within the concept of the MRA framework this requires the inference engine 26 illustrated in FIG. 2. Although both algorithms require R-wave detection as a first step, the required processing power for subsequent processing steps is typically highest for the P-wave power algorithm. Consequently, in an exemplary embodiment of the invention the CSM and P-wave power algorithms are combined and the P-waver power $AF_{index}$ is calculated only if the CSM algorithm does not provide crisp rhythm discrimination between normal sinus rhythm and AF. The advantage of this approach is that only a small percentage of all cases require analysis of both the CSM algorithm and the P-wave power algorithm results.

Figure 7:
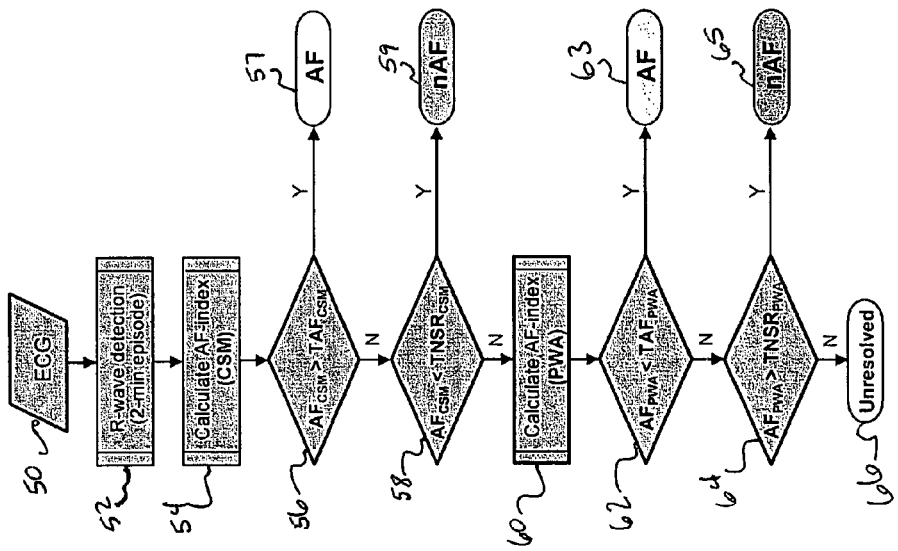
FIG. 7 is a flow chart of a process for combining the CSM and P-wave power algorithms to detect AF in a patient according to the present invention.

FIG. 7 is a flow chart of an exemplary process for combining the CSM and P-wave power algorithms according to an exemplary embodiment of the invention. At step 50 an ECG is performed on a patient. R-waves are detected during step 52 for predetermined time intervals. The set of steps 54 to 59 pertains to AF determinations based on the CSM algorithm, and the set of steps 60 to 65 pertains to AF determinations based on the P-wave power algorithm. Although a preferred embodiment carries out the CSM algorithm steps first the P-wave power algorithm steps can be carried out before or simultaneous with the CSM algorithm steps. For example, in an embodiment that carries out the P-waver power algorithm first, steps 60 to 65 in FIG. 7 would be performed before steps 54 to 59.

Figure 8:
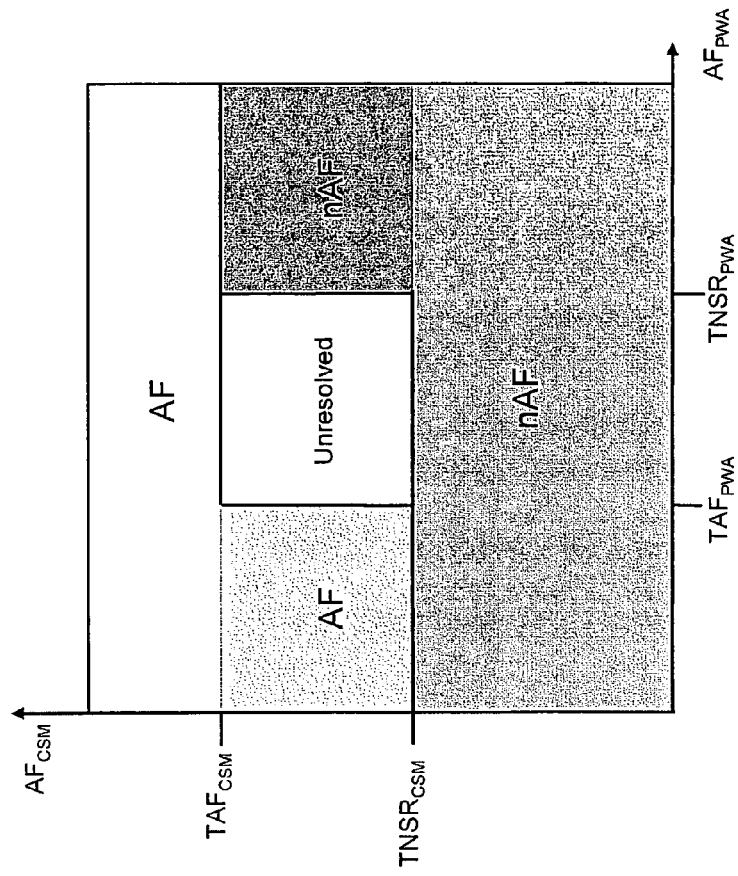
FIG. 8 is a graph of a solution space plotting CSM algorithm solutions on the vertical axis against P-wave power algorithm solutions on the horizontal axis according to the present invention.

The CSM algorithm steps 54 to 59 and the P-wave power algorithm steps 60 to 65 are described with reference to FIG. 8, which is a graph of a solution space plotting the CSM algorithm solutions on the vertical axis against the P-wave power algorithm solutions on the horizontal axis. In step 54, the AF index is calculated using the previously discussed CSM algorithm. However, there is a region at which the CSM-derived AF index is not sufficiently conclusive regarding the presence of AF in a patient. In step 56, a decision is made based on whether the CSM-derived AF index is greater than a predetermined value $TAF_{CSM}$. If the AF index is greater than $TAF_{CSM}$ then the process ends at step 57 with a determination that the patient is experiencing AF. If the AF index is less than $TAF_{CSM}$, the process advances to step 58 during which a decision is made based on whether the CSM-derived AF index is less than a predetermined value $TNSR_{CSM}$. If the AF index is less than $TNSR_{CSM}$ then the process ends at step 59 with a determination that the patient is definitely not experiencing AF.

Reviewing FIG. 8, between the areas above $TAF_{CSM}$ and below $TNSR_{CSM}$ is the unresolved region for which the CSM-derived AF index does not conclusively determine whether a patient is experiencing AF. If the CSM-derived AF index is inconclusive in this respect, then the process in FIG. 7 advances to step 60 at which the AF index is calculated using the previously described P-wave power algorithm (PWA). In step 62, a decision is made based on whether the PWA-derived AF index is greater than a predetermined value $TAF_{PWA}$. If the AF index is greater than $TAF_{PWA}$ then the process ends at step 63 with a determination that the patient is experiencing AF. If the AF index is less than $TAF_{PWA}$, the process advances to step 64 during which a decision is made based on whether the CSM-derived AF index is less than a predetermined value $TNSR_{PWA}$. If the AF index is less than $TNSR_{PWA}$ then the process ends at step 65 with a determination that the patient is definitely not experiencing AF. If the AF index is greater than $TNSR_{PWA}$ then the method ends at step 66 with an unresolved determination.

EXAMPLE 3

Using the Holter ECG from Examples 1 and 2, the method previously described with reference to FIG. 7 was performed, with determinations being made using the CSM-derived AF index before using the PWA-derived AF index. The result of this CSM/PWP algorithm detection performance for AF is summarized in Table III.

Performance was determined by calculating the sensitivity and specificity of detection results against expert data. An exact match of test and annotation data resulted in an average sensitivity and specificity of 93.6% and 96.6% (Se/Sp improvement of 0.66% and 1.61% vs. CSM alone) whereas when allowing for a detection deviation of ±1 episode (2 min) the average Se/Sp increased to 99% and 97.8% (Se/Sp improvement of 0.26% and 0.71% vs. CSM alone). The CSM $AF_{index}$ score was within the uncertainty band (55-145) in 9.51% of all 2 min episodes (10637) requiring execution of the PWP algorithm (PWP threshold=130).

TABLE III

Combined Holter CSM/PWP analysis results

| HOLTER RECORDING | AF [%] | NUMBER OF EPISODES | TRUE POSITIVE | TRUE NEGATIVE | FALSE POSITIVE | FALSE NEGETIVE | SENSITIVITY [%] | SPECIFICITY [%] |
|---|---|---|---|---|---|---|---|---|
| 2 | 8 | 716 | 50 | 663 | 0 | 0 | 100 | 100 |
| 3 | 0 | 716 | 0 | 716 | 0 | 0 | — | 100 |
| 7 | 3 | 705 | 18 | 685 | 0 | 0 | 100 | 100 |
| 9 | 61 | 716 | 456 | 260 | 0 | 0 | 100 | 100 |
| 11 | 36 | 716 | 252 | 464 | 0 | 0 | 100 | 100 |
| 12 | 3 | 665 | 11 | 614 | 2 | 1 | 91.7 | 99.7 |
| 15 | 100 | 716 | 716 | 0 | 0 | 0 | 100 | — |
| 17 | 0 | 714 | 0 | 714 | 0 | 0 | — | 100 |
| 18 | 38 | 716 | 267 | 449 | 0 | 0 | 100 | 100 |
| 19 | <1 | 716 | 1 | 712 | 2 | 0 | 100 | 99.7 |
| 20 | 62 | 716 | 487 | 228 | 0 | 0 | 100 | 100 |
| 22 | 0 | 718 | 0 | 509 | 207 | 0 | — | 71.1 |
| 24 | 13 | 718 | 74 | 599 | 4 | 1 | 98.7 | 99.3 |
| 26 | <1 | 655 | 0 | 653 | 0 | 0 | — | 100 |
| 27 | 0 | 712 | 0 | 710 | 0 | 0 | — | 100 |

Average sensitivity 99%

Average specificity 97.8%

EXAMPLE 4

Using the Holter ECG from Examples 1 to 3, the method previously described with reference to FIG. 7 was performed, although in this example determinations were made using the CSM-derived AF index after using the PWA-derived AF index. The result of this PWP/CSM algorithm detection performance for AF is summarized in Table IV.

An exact match of test and annotation data resulted in an average sensitivity and specificity of 97.6% and 98.9% (Se/Sp improvement of 0.9% and 1.1% vs. PWP alone) whereas when allowing for a detection deviation of ±1 episode (2 min), the average Se/Sp increased to 100% (no false negatives) and 99.5% (Se/Sp improvement of 0.16% and 0.31% vs. PWP alone). The PWP $AF_{index}$ score was within the uncertainty band (80-180) in 7.6% of all 2 min episode requiring execution of the CSM algorithm (CSM threshold=100).

TABLE IV

Combined Holter PWP/CSM analysis results

| HOLTER RECORDING | AF [%] | NUMBER OF EPISODES | TRUE POSITIVE | TRUE NEGATIVE | FALSE POSITIVE | FALSE NEGETIVE | SENSITIVITY [%] | SPECIFICITY [%] |
|---|---|---|---|---|---|---|---|---|
| 2  | 8   | 716 | 50  | 657 | 6 | 0 | 100 | 99.1 |
| 3  | 0   | 716 | 0   | 716 | 0 | 0 | —   | 100  |
| 7  | 3   | 705 | 18  | 679 | 6 | 0 | 100 | 99.1 |
| 9  | 61  | 716 | 456 | 260 | 0 | 0 | 100 | 100  |
| 11 | 36  | 716 | 252 | 464 | 0 | 0 | 100 | 100  |
| 12 | 3   | 665 | 12  | 616 | 0 | 0 | 100 | 100  |
| 15 | 100 | 716 | 716 | 0   | 0 | 0 | 100 | —    |
| 17 | 0   | 714 | 0   | 710 | 4 | 0 | —   | 99.4 |
| 18 | 38  | 716 | 267 | 449 | 0 | 0 | 100 | 100  |
| 19 | <1  | 716 | 1   | 712 | 2 | 0 | 100 | 99.7 |
| 20 | 62  | 716 | 487 | 221 | 7 | 0 | 100 | 97.9 |
| 22 | 0   | 718 | 0   | 712 | 4 | 0 | —   | 99.4 |
| 24 | 13  | 718 | 75  | 596 | 7 | 0 | 100 | 98.8 |
| 26 | <1  | 655 | 0   | 653 | 0 | 0 | —   | 100  |
| 27 | 0   | 712 | 0   | 710 | 0 | 0 | —   | 100  |

Average sensitivity 100%
Average specificity 99.5%

Having described exemplary methods for carrying out AF detection, it should be recognized that the principles of the present invention can be applied to detection of other irregularities in a heart beat pattern. For example, although the previously discussed methods relate to analysis of P-waves as indicators of atrial contraction, the same process of signal averaging an ECG can be used to detect asynchronous ventricle relaxation. In such an embodiment, the SAECG would reveal intra-wave differences between the regions surrounding the T-wave during synchronous and asynchronous ventricle relaxation. T-wave analysis can be carried out to detect T-wave alternans, or ischemia, to name some examples. Other intra-wave analyses can also be performed using the SAECG to detect different irregularities. For example, instead of utilizing the R-waves as a trigger for aligning and averaging heartbeat complexes in an ECG, the P-waves can be used as the trigger point of reference and the analyzed segment can be the R-wave, the T-wave, or the entire QRS complex.

It should also be recognized that although the present invention as previously described utilizes signal averaging to discriminate between normal sinus rhythm and AF, other statistical calculations can be utilized to discriminate between normal and irregular beat patterns. For example, instead of calculating the average or mean signal other statistical calculations such as signal strength in a predetermined percentile range, a signal median, variability from the signal average, variability from the signal median, standard deviation from the signal average, and standard deviation from the signal median, to name just a few, can be utilized to make effective detections.

The detection methods of the present invention can be performed by a variety of therapeutic and diagnostic devices. According to one embodiment of the invention a therapeutic or diagnostic device can be equipped with or connected to either an implantable or an external recorder that is programmed to record loops of ECG signals. Depending on the size and capacity for the recorder, ECG signals are recorded for intervals of predetermined time and then are erased as new ECG signals are recorded over old signals. The therapeutic or diagnostic device is further equipped with or attached to a processor that is configured to carry out a detection method of the present invention. In the event that the processor detects AF or another irregularity, the processor will carry out a programmed function.

Returning to FIG. 2, a therapeutic or diagnostic device according to an embodiment of the invention includes a processor that is configured to perform MRA 22 for each time scale and produces characterization vectors 24 that are input into the inference engine 26 which is also included in the device. As previously discussed, the inference engine 26 combines all characterization vectors into the decision vector 28 that contains diagnostic information and certainty levels, and can be used to automatically control a therapy, trigger internal storage of signals, actuate a communication device, actuate an alerting device or other communication signal such as an audible alarm to notify the patient or a physician, or perform other procedures based on the information.

There are three general categories of devices that can be equipped with a recorder, a memory, and a processor to receive ECG signals and carry out the detection methods of the present invention. The first type of device is an external apparatus that receives ECG signals when attached to a patient. The external apparatus can be a portable, wearable machine that includes a processor and is coupled to receive an ECG as an input signal.

The second type of device is any implantable medical device (IMD) that is minimally invasive, meaning that the device is implanted in a relatively non-invasive body area away from the heart. One example of a non-invasive IMD is the Medtronic Reveal™ insertable loop recorder, which is a form of implantable monitor that is intended to be implanted subcutaneously and has a pair of sense electrodes spaced apart, e.g. by about 47 mm, on the device housing. The electrodes are used to pick up the cardiac far field EGM which in this case is characterized as a "subcutaneous ECG". The Reveal™ insertable loop recorder samples and records one or more segment (depending on the programmed operating mode) of the far-field EGM or subcutaneous ECG signals. The recorder memory capacity is limited, so the segments of the EGM episode data that are stored in memory can be written over with new EGM episode data when the memory is full. However, according to an embodiment of the invention, over-writing can be halted when the processor detects AF. The most recently stored segment or segments of episode data are transmitted via an uplink telemetry transmission to an external programmer when a memory interrogation telemetry session is initiated by a physician using the programmer. Aspects of the Reveal™ insertable loop recorder are disclosed in commonly assigned PCT publication WO98/02209 and in U.S. Pat. Nos. 5,987,352 and 6,230,059.

The third type of device is an IMD such as a pacemaker or other diagnostic device that detects an EGM directly from the heart. An exemplary embodiment of such an IMD is an atrial chamber pacemaker that records as the primary signal the atrial EGM that includes a ventricular component that can be separated and serve as a trigger for beat-to-beat averaging of the atrial component. Another exemplary embodiment is a dual chamber pacemaker having leads attached to an atrium and a ventricle (epicardial, endocardial, or both combined). The dual chamber pacemaker can separate atrial and ventricular signals, and then utilize the ventricular signal as a trigger to cause the processor to average the atrial signal. Yet another exemplary embodiment is a device that includes electrodes attached to multiple heart locations, e.g. left and right, and signals from each electrode can be utilized as a trigger for the processor to average the signals from the other electrode(s).

The methods and apparatuses of the present invention therefore introduce an MRA framework that implements digital signal processing technology into heart beat irregularity detection processes that include event-based analysis algorithms. By combining digital signal processing technology with event-based algorithms, an EGM is unraveled and normal patterns can be discriminated from irregular patterns by focusing on wave morphology.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A method for detecting a cardiac arrhythmia from an electrocardiogram, the method comprising a series of wave morphology analysis steps, comprising:
    identifying a plurality of wave patterns that are repeated in the electrocardiogram during a predetermined time interval, each wave pattern being indicative of an individual heartbeat;
    extracting a heartbeat complex that corresponds to each of the identified wave patterns;
    identifying a key region within each heartbeat complex that is morphologically altered in the event of the cardiac arrhythmia;
    calculating a statistical measurement of an ensemble of the key regions from each of the heartbeat complexes; and
    determining from the statistical measurement whether the cardiac arrhythmia occurred during the predetermined time interval.

2. A method according to claim 1, wherein the wave patterns in the electrocardiogram comprise R-waves.

3. A method according to claim 1, wherein the cardiac arrhythmia comprises an episode of atrial fibrillation.

4. A method according to claim 3, wherein the key region morphologically altered in the event of the cardiac arrhythmia comprises a P-wave region.

5. A method according to claim 1 wherein the statistical measurement comprises a signal average of the key regions from each of the heartbeat complexes.

6. A method according to claim 5, wherein the cardiac arrhythmia comprises atrial fibrillation, and the statistical measurement comprises a signal average of the P-wave regions from each of the heartbeat complexes.

7. A method according to claim 3, further comprising a series of event-based analysis steps for detecting atrial fibrillation, comprising:
    defining a signature metric for atrial fibrillation representative of a distribution of data points during atrial fibrillation episodes;
    determining an interval for each time period that occurs between successive ventricular heartbeats;
    plotting each succeeding interval as a data point in a scatter-plot;
    developing a discriminatory metric signifying a degree of sparseness or clustering of the data points in the scatter-plot; and
    concluding that atrial fibrillation occurred if the discriminatory metric satisfies the atrial fibrillation signature metric representative of data points during atrial fibrillation.

8. A method according to claim 7, wherein the scatter-plot comprises a Lorenz plot having an origin, and the plotting step further comprises assigning an abscissa value and an ordinate value referenced to the origin of the Lorenz plot to each data point, whereby the data point comprises a two-dimensional (2-D) data point.

9. A method according to claim 8, further comprising the steps of:
    defining 2-D bins of the Lorenz plot with reference to the origin of the Lorenz plot; and
    correlating each 2-D data point of the Lorenz plot with a bin of the Lorenz plot that the 2-D data point falls within, and wherein,
        the step of developing a discriminatory metric further comprises:
            counting the number of 2-D data points added to each bin over the segment,
            determining the highest number of 2-D data points in a single bin as a MaxB,
            counting the number of bins containing at least one 2-D data point as LowC,
            counting the number of bins containing at least one 2-D data point and a predetermined number of 2-D data points as a nozC, and
            calculating a cluster signature metric (CSM) using the formula:

CSM=nozC+lowC−MaxB, the step of defining an atrial fibrillation signature metric comprises establishing a CSM signature metric for atrial fibrillation; and
        the concluding step comprises declaring atrial fibrillation if the derived CSM satisfies the CSM signature metric for atrial fibrillation.

10. A method according to claim 7, wherein the event-based analysis steps for detecting atrial fibrillation are performed prior to the series of wave morphology analysis steps.

11. A method according to claim 7, wherein the event-based analysis steps for detecting atrial fibrillation are performed following the series of wave morphology analysis steps.

12. A method according to claim 1, wherein the wave patterns that are repeated in the electrocardiogram comprise P-waves.

13. A method according to claim 1, wherein the key region that is morphologically altered in the event of the cardiac arrhythmia comprises at least one T-wave region.

14. A method according to claim 13, wherein the cardiac arrhythmia comprises a T-wave alternans condition.

15. A method according to claim 13, wherein the cardiac arrhythmia comprises one of: an acute ischemic episode, a silent ischemia episode, a chronic ischemic condition.

16. A method according to claim 1, wherein the statistical measurement from which the cardiac arrhythmia occurrence is detected is selected from the group consisting of a signal average, a signal median, variability from the signal average, variability from the signal median, standard deviation from the signal average, standard deviation from the signal median, a signal strength in a predetermined percentile range.

17. A method according to claim 1, further comprising the steps of:
   recording the electrocardiogram into a memory using a loop recorder; and
   recording new electrocardiograms over previously recorded electrocardiograms unless it is determined from the statistical measurement that the cardiac arrhythmia occurred during the predetermined time interval.

18. A method according to claim 1, further comprising the step of:
   producing a communication signal after determining from the statistical measurement that the cardiac arrhythmia occurred during the predetermined time interval.

19. An apparatus for detecting a cardiac arrhythmia from an electrocardiogram, comprising:
   a processor that is coupled to receive the electrocardiogram, and is configured in response thereof to perform a series of wave morphology analysis steps, comprising:
      identifying a plurality of wave patterns that are repeated in the electrocardiogram during a predetermined time interval, each wave pattern being indicative of an individual heartbeat;
      extracting a heartbeat complex that corresponds to each of the identified wave patterns;
      identifying a key region within each heartbeat complex that is morphologically altered in the event of the cardiac arrhythmia;
      calculating a statistical measurement of an ensemble of the key regions from each of the heartbeat complexes; and
      determining from the statistical measurement whether the cardiac arrhythmia occurred during the predetermined time interval.

20. An apparatus according to claim 19, wherein the wave patterns that are repeated in the electrocardiogram comprise R-waves.

21. An apparatus according to claim 19, wherein the cardiac arrhythmia comprise an atrial fibrillation condition.

22. An apparatus according to claim 20, wherein the key region that is morphologically altered in the event of the cardiac arrhythmia comprises a P-wave region.

23. An apparatus according to claim 19, wherein the statistical measurement from which the cardiac arrhythmia occurrence is detected is a signal average of the key regions from each of the heartbeat complexes.

24. An apparatus according to claim 22, wherein the cardiac arrhythmia is atrial fibrillation, and the statistical measurement from which the cardiac arrhythmia occurrence is detected is a signal average of the P-wave regions from each of the heartbeat complexes.

25. An apparatus according to claim 21, wherein the processor is further configured to perform a series of event-based analysis steps for detecting atrial fibrillation, comprising:
   defining a signature metric for atrial fibrillation representative of a distribution of data points during atrial fibrillation episodes;
   determining an interval for each time period that occurs between successive ventricular heartbeats;
   plotting each succeeding interval as a data point in a scatter-plot;
   developing a discriminatory metric signifying a degree of sparseness or clustering of the data points in the scatter-plot; and
   concluding that atrial fibrillation occurred if the discriminatory metric satisfies the atrial fibrillation signature metric representative of data points during atrial fibrillation.

26. An apparatus according to claim 25, wherein the scatter-plot is a Lorenz plot having an origin, and the plotting step further comprises assigning an abscissa value and an ordinate value referenced to the origin of the Lorenz plot to each data point, whereby the data point is a two-dimensional (2-D) data point.

27. An apparatus according to claim 26, wherein the processor is further configured to perform, as part of the series of event-based analysis steps for detecting atrial fibrillation, the steps of:
   defining 2-D bins of the Lorenz plot with reference to the origin of the Lorenz plot; and
   correlating each 2-D data point of the Lorenz plot with a bin of the Lorenz plot that the 2-D data point falls within, and wherein,
      the step of developing a discriminatory metric further comprises:
         counting the number of 2-D data points added to each bin over the segment,
         determining the highest number of 2-D data points in a single bin as a MaxB,
         counting the number of bins containing at least one 2-D data point as LowC,
         counting the number of bins containing at least one 2-D data point and a predetermined number of 2-D data points as a nozC, and
         calculating a cluster signature metric (CSM) using the formula:

$CSM = nozC + lowC - MaxB$, the step of defining an atrial fibrillation signature metric comprises establishing a CSM signature metric for atrial fibrillation; and
      the concluding step comprises declaring atrial fibrillation if the derived CSM satisfies the CSM signature metric for atrial fibrillation.

28. An apparatus according to claim 25, wherein the processor is configured to perform the event-based analysis steps for detecting atrial fibrillation prior to performing the series of wave morphology analysis steps.

29. An apparatus according to claim 25, wherein the processor is configured to perform the event-based analysis steps for detecting atrial fibrillation following the series of wave morphology analysis steps.

30. An apparatus according to claim 19, wherein the wave patterns that are repeated in the electrocardiogram are P-waves.

31. An apparatus according to claim 19, wherein the key region that is morphologically altered in the event of the cardiac arrhythmia is a T-wave region.

32. An apparatus according to claim 31, wherein the cardiac arrhythmia is T-wave alternans.

33. An apparatus according to claim 31, wherein the cardiac arrhythmia comprises an ischemic event.

34. An apparatus according to claim 19, wherein the statistical measurement from which the cardiac arrhythmia occurrence is detected is selected from the group consisting of a signal average, a signal median, variability from the signal average, variability from the signal median, standard deviation from the signal average, standard deviation from the signal median, and signal strength in a predetermined percentile range.

35. An apparatus according to claim 19, wherein the apparatus is an implantable medical device.

36. An apparatus according to claim 35, wherein the implantable medical device is a pacemaker device.

37. An apparatus according to claim 19, further comprising:
a programmable memory that is coupled to the processor and that records the electrocardiogram, wherein the memory is programmed to record new electrocardiograms over previously recorded electrocardiograms unless it is determined from the statistical measurement that the cardiac arrhythmia occurred during the predetermined time interval.

38. An apparatus according to claim 19, further comprising:
a communication device coupled to the programmer to produce a communication signal after it is determined from the statistical measurement that the cardiac arrhythmia occurred during the predetermined time interval.

* * * * *